United States Patent
Dellanno

(10) Patent No.: US 7,819,831 B2
(45) Date of Patent: Oct. 26, 2010

(54) DEVICES FOR ALLEVIATING BACK STRAIN AND BACK PAIN

(76) Inventor: Ronald P. Dellanno, 532 Broad St., Bloomfield, NJ (US) 07003

( * ) Notice: Subject to any disclaimer, the term of this patent is extended or adjusted under 35 U.S.C. 154(b) by 545 days.

(21) Appl. No.: 11/363,552

(22) Filed: Feb. 27, 2006

(65) Prior Publication Data

US 2007/0199125 A1   Aug. 30, 2007

(51) Int. Cl.
  *A61F 5/37* (2006.01)
  *A61G 1/00* (2006.01)
(52) U.S. Cl. .................. 602/19; 128/870; 128/875; 224/158; 224/160; 450/2; 450/96
(58) Field of Classification Search .................. 602/19; 128/95.1, 96.1, 99.1, 102.1, 105.1, 869, 873–874, 128/876, 875; 224/157–161, 628, 631; 450/2, 450/96, 114; 2/467, 44, 92
See application file for complete search history.

(56) References Cited

U.S. PATENT DOCUMENTS

| | | | |
|---|---|---|---|
| 4,952,192 A * | 8/1990 | Burke ......................... 450/15 |
| 5,547,461 A * | 8/1996 | Levis .......................... 602/19 |
| 6,179,187 B1 | 1/2001 | Lemire et al. |
| 6,364,186 B1 | 4/2002 | Gilmour et al. |
| 6,820,783 B2 | 11/2004 | Beale |
| 6,840,916 B2 * | 1/2005 | Kozersky ..................... 602/19 |
| 6,852,087 B1 * | 2/2005 | Dainese ....................... 602/19 |
| 2004/0149790 A1 * | 8/2004 | Kassai et al. ................ 224/160 |

* cited by examiner

Primary Examiner—Patricia M Bianco
Assistant Examiner—Keri J Nicholson
(74) Attorney, Agent, or Firm—Klauber & Jackson, LLC

(57) ABSTRACT

A device for relieving back strain for a user who is supporting a substantial weight which is off the user's vertical body axis at his or her front side. The device alleviates the aforementioned difficulties by utilizing the otherwise detrimental forces generated by the off-axis weight to press a rigid plate behind and adjacent to the spine of the device user against the user's spine. This rigid plate is preferably contoured to mirror the shape of the human spine. The device in one embodiment is used as a baby carrier. In another it is used with an abdominal support during pregnancy. In a third embodiment it provides support for the breasts of large breasted women.

26 Claims, 8 Drawing Sheets

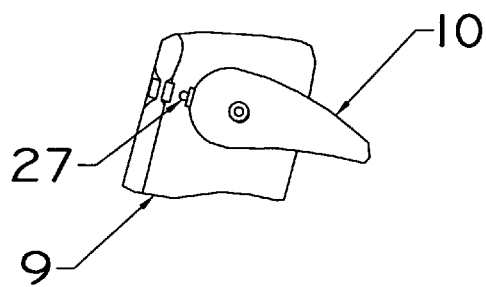
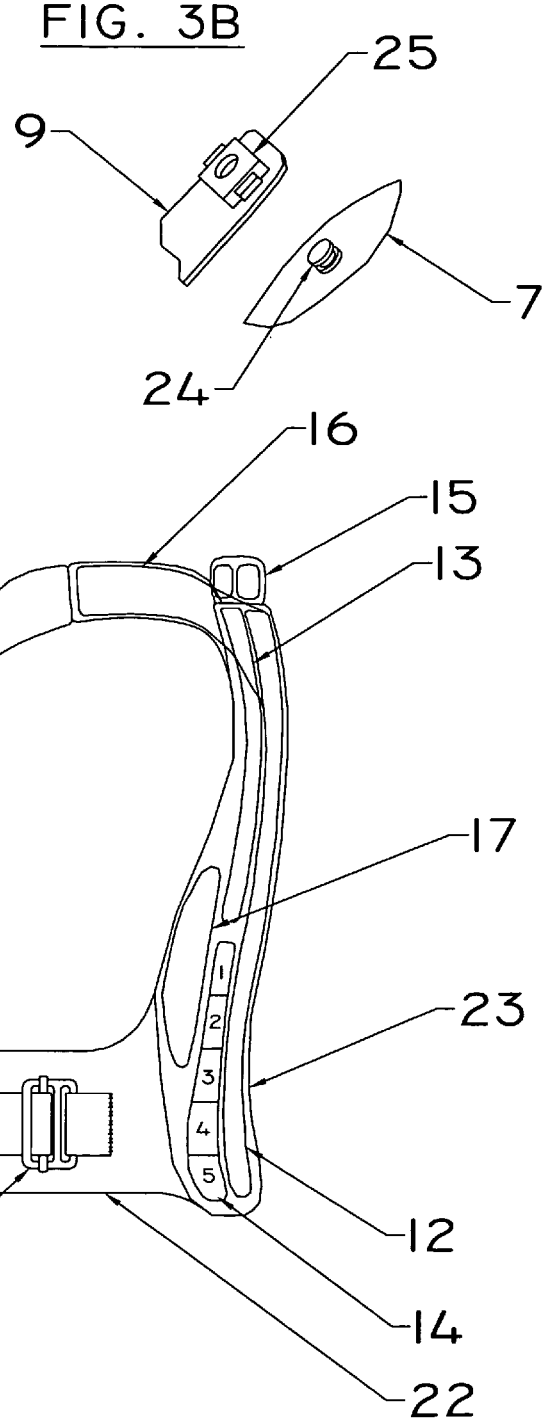

DEVICES FOR ALLEVIATING BACK STRAIN AND BACK PAIN

FIELD OF THE INVENTION

This invention relates generally to devices for alleviating back strain and back pain, and more specifically relates to apparatus of this type which is applicable where an individual is supporting a substantial weight which is off the user's vertical body axis at his or her front side.

BACKGROUND OF THE INVENTION

There are numerous instances in which individuals by virtue of physical conditions or for their own convenience are obliged to support substantial weight which is off the user's vertical body axis at his or her front side. One such common environment to which the present invention is applicable is the increasing use of baby carriers. The current designs for the carriers which are commercially available permit mothers and fathers to carry their babies on their chests while allowing their arms and hands to be free. Typically the baby is placed in a sack (which may be herein referred to as a "papoose") intended to be secured at the front side of the parent. Straps are used to attach the papoose around the shoulders and back of the parent so as to secure the baby to the parent's chest. These designs often produce fatigue strains on the spine as the weight of the baby causes shear, moment, and compressive forces at the spine. This is particularly significant for persons who already suffer from back pain due to spinal conditions like scoliosis and/or degenerative joint disease of the discs, facets and vertebral bodies.

A further natural condition yielding similar harmful back effects occurs during especially the latter stages of pregnancy. The enlargement of the abdominal region creates an increasing off vertical body axis weight, the consequences of which are very similar to those involved in use of the baby carrier as aforementioned. Numerous designs of abdominal supports have been provided over the years in an effort to alleviate this problem by providing some type of support wearable by the pregnant woman to relieve these effects. In much of this prior art it is found that relief is only provided relative to the area of pain, usually the lumbar spine. This leaves the thoracic spine and shoulders vulnerable to shear and compression forces.

A third area to which the principles of the present invention are applicable arises in the instance of large breasted women. The need to support such large breasts generates harmful strain forces through the spine similar to the case of the baby in the papoose of the baby carrier. This again is in essence a strain caused by the presence of the substantial off vertical axis weight, and the consequences to the individual are similar as in the two prior instances discussed above.

SUMMARY OF THE INVENTION

Now in accordance with the present invention a device is provided which alleviates the aforementioned difficulties by utilizing the otherwise detrimental forces generated by the off-axis weight to press a monolithic rigid contoured plate behind and adjacent to the spine of the device user against the user's spine. This rigid plate is preferably contoured to mirror the shape of the human spine, in accordance with principles discussed in a number of my prior patents, including U.S. Nos. 5,290,091; 5,580,124 and 5,769,489, the entire disclosures of which are incorporated by reference herein.

Thus in accordance with the principles of the invention, a device is provided for relieving back strain for a user who is supporting a substantial weight which is off the user's vertical body axis at his or her front side. The device includes a waist encirclement means securable about the waist of the user. A monolithic rigid plate contoured to mirror and engage with the shape of the thoracic kyphosis and lumbar lordosis, is positioned at the back of the user, and is restrained in its degree of possible upward displacement by the waist encirclement means. Flexible strapping means are connected at the rear of the user to exert an upward and forward force at the plate when the strapping is tensioned. The strapping means extend over the shoulders from the rear side of the user, and weight support means are secured to the strapping means at the front of the user for supporting the off-axis weight. The flexible strapping means bear a substantial part of the weight imposed upon the weight support means and are therefore tensioned by the weight. The resulting forces generated by the tensioned strapping means act to press the contoured plate toward the user's back. This exerts beneficial pressure against the thoracic kyphosis and lumbar lordosis to relieve the back strain.

The flexible strapping means can be directly connected toward the top end of the rigid plate, as for example by passing through slots in the plate or otherwise affixed, and the upward displacement of the monolithic rigid plate can be restrained in a similar manner by direct or indirect attachment of the bottom end of the plate to the waist encirclement means. Thus in an indirect attachment arrangement a back panel of fabric or the like can extend upwardly from the rear side of the waist encirclement means, with the flexible strapping means extending from the back panel over the shoulders of the user and down the front of the user. The monolithic rigid plate is again positioned relative to the tensioned strapping means and back panel such that forces generated by the tensioned strapping means and back panel act to press the plate toward the user's back. The rigid plate in one arrangement of this type can be directly attached to the back panel or the plate can be snugly fitted into a pocket or void formed in or at the panel.

In one embodiment of the invention, the weight support means may comprise a baby carrier. In another instance it may comprise an abdominal support for use in the latter stages of pregnancy; and in yet instance another may comprise a brassiere for use by large breasted women.

The shear, moment and compressive forces generated by the weight of the baby, or by the protruding abdomen, or by the large heavy breasts are effectively transferred to the contoured rigid plate by the straps that connect the weight support means to the said plate. These straps connect over the shoulders to the upper portion of the plate or to an enclosure for the plate, while the waist encirclement means can connect to the lower portion of the plate or to an enclosure for the plate. The effect is to spare the spine the strain forces that would cause relative displacement between the vertebrae of the spine and prevent back pain to the person using the inventive device.

In addition, this new brace is designed to ameliorate pressure to the shoulders as well, by offering strap attachments that protect the shoulder from compression forces that could injure the brachial arteries and nerves that pass through the shoulder region. The strap attachments may be stiff in nature or can be made of similar materials as the rigid plate.

The monolithic rigid plate will have the shape of the human contour starting from the top of the thoracic spine and ending at the level of the waist. The contour will follow the shape of the thoracic kyphosis and lumbar lordosis. The lumbar section can be made of the same rigid material that is used in the thoracic spine section or can utilize a multiple air bladder system that is designed to support the entire lumbar lordosis or direct the support to specific more precise areas of the lumbar curve. There can be one single air bladder or multiple air bladders and/or lordosis pad chambers that may be used separately or in combination to achieve maximum comfort in the lower back area. The lordosis pads can be made of foam or other materials that perform a similar function. These materials are known to those skilled in the art. These said pads can be used alone or in combination with the air bladders to accomplish the desired support.

BRIEF DESCRIPTION OF DRAWINGS

The invention is diagrammatically illustrated, by way of example, in the drawings appended hereto in which:

FIG. 3A shows the device in FIG. 2 without the device user and infant;

FIG. 3B is a detailed view of the latch mechanism used in the FIG. 3A device;

FIG. 3C is a detailed view illustrating how the "horse collar" of the device is attached to the "papoose";

DESCRIPTION OF PREFERRED EMBODIMENTS

Figures 1A, 1B:
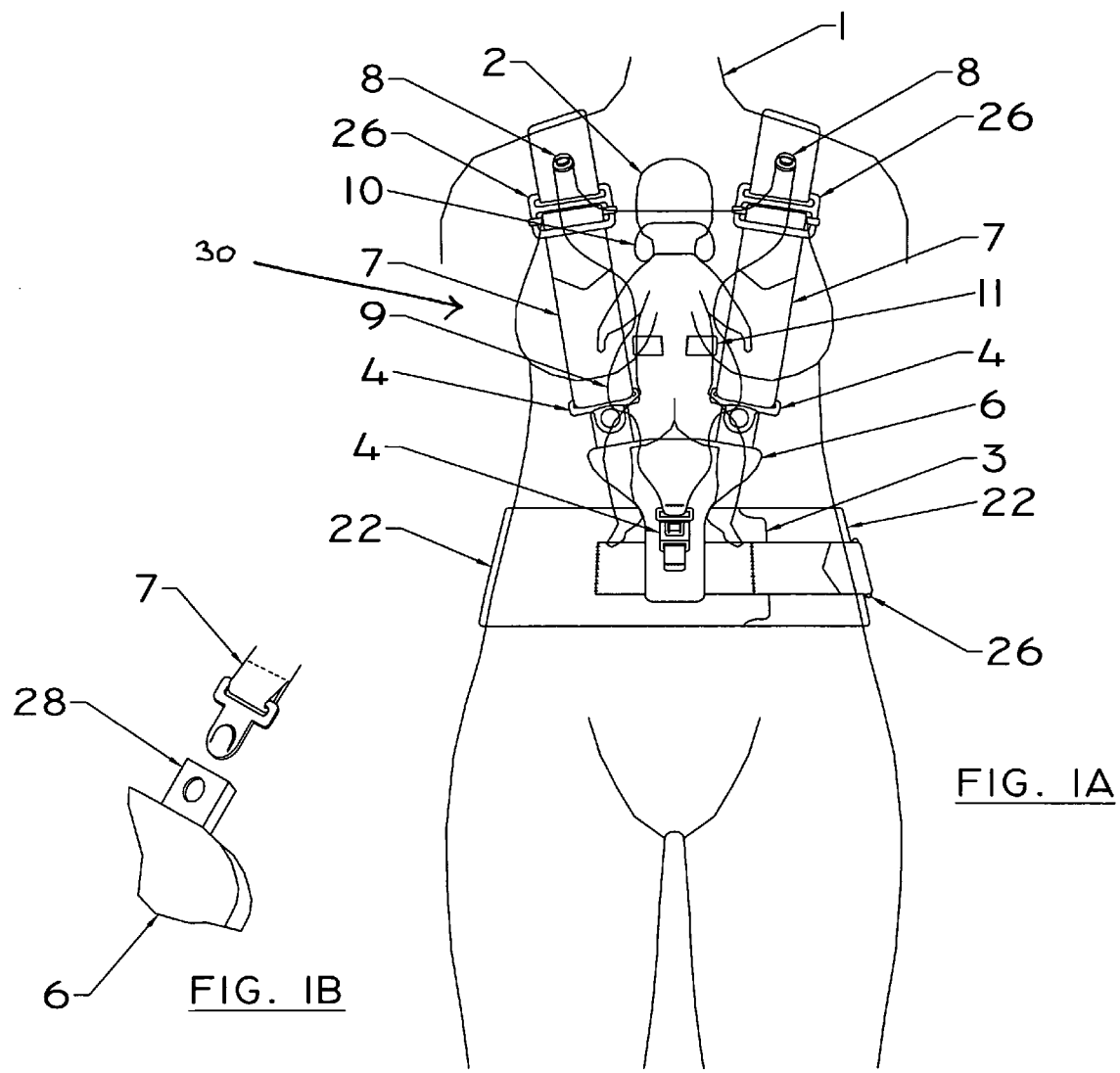
FIG. 1A is a front perspective view of the invention being utilized in connection with a representative person carrying an infant in a baby carrier.
FIG. 1B is a detailed view of the quick release buckle system of the FIG. 1A device.
Figure 2:
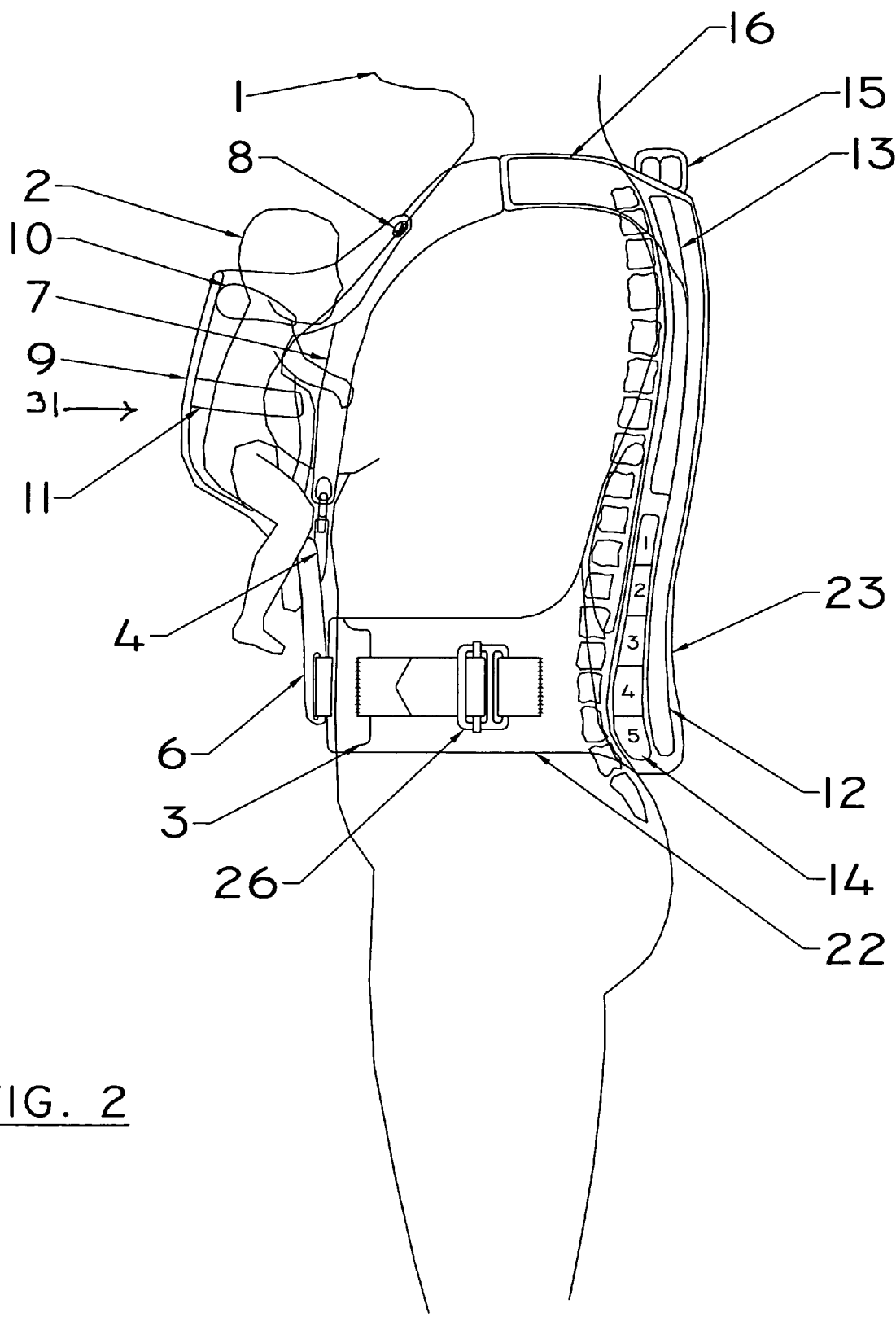
FIG. 2 is a side perspective view of the device of FIG. 1A.
Figure 4:
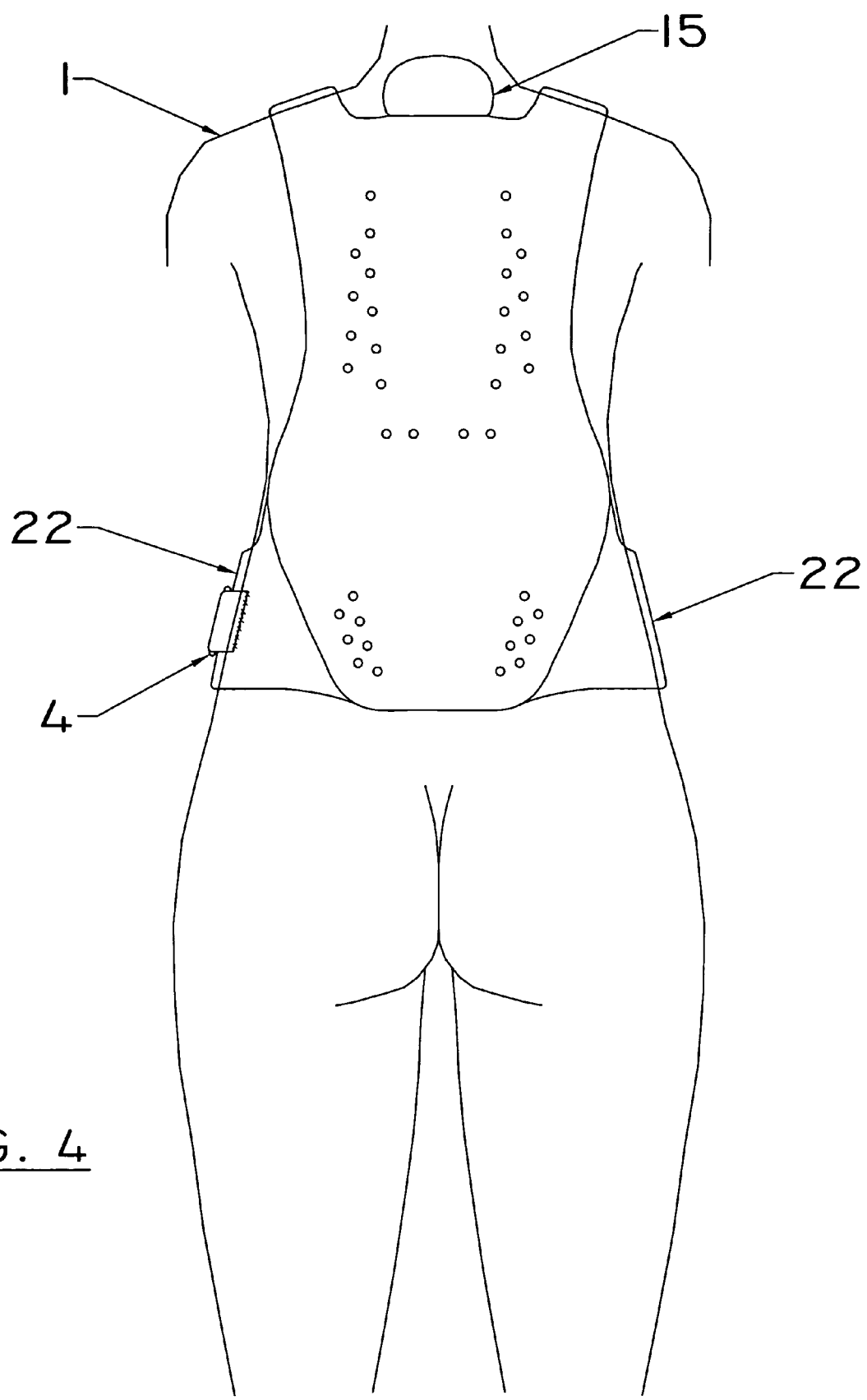
FIG. 4 is a rear perspective view of the device of FIG. 1.

In FIGS. 1A and 1B a front perspective view appears of a first embodiment of the present device 30 in accordance with the invention. These Figures may be viewed simultaneously with FIGS. 2, 3A, 3B, 3C and 4 in order to better appreciate the structure of device 30. As seen therein the device 30 includes a waist encirclement means 22 which encircles in secure belt-like fashion the waist of a user 1 of the device. The means 22 can be adjusted to fit by VELCRO (hook and loop) straps 3. A slide loop retaining buckle 26 (FIG. 2) extends from the side of means 22 around to the front of user 1. A back panel 23 extends upwardly from the rear side of waist encirclement means 22 and is formed at its upward part into flexible strapping means 16 which extend from the back panel over the shoulders of user 1 and down the front of the user. Stiffening strap attachments may be provided where the strapping means 16 passes over the user's shoulders. Weight support means 31 are secured to the strapping means 16 at the front of the user for supporting a weight such as in the present embodiment an infant or baby carrier. The weight support means 31 in the instance of this first embodiment takes the form of a hammock-like device for the infant 2, conveniently referred to herein as "papoose" 9. The papoose 9 is attached to strapping 16 by conventional latch mechanisms 8 (FIG. 3A), which include (FIG. 3B) a retaining stud 24 and buckle 25. Infant 2 is supported on a lower support straddle 6 to which connections are made by buckles 4. An infant support collar 10 at the top of the support rather resembles "a horse collar" and is a removable element via a button snap 27. A tether strap is provided at 11. The lower end of papoose 9 is also secured to the front of encirclement means 22 by a simple buckle arrangement as shown in FIG. 1B where a conventional latch mechanism is part of a quick release buckle system 28 as known in the art. One end of this latch mechanism is on an adjustable strap 7 to enable adjustment for the person or infant size.

It will be evident that the flexible strapping means 16 bears a substantial part of the weight present at the weight support means 31 and the strapping means is thereby tensioned from this weight, in turn tensioning the back panel 23. In accordance with the principles of the invention a monolithic rigid plate 12 is positioned at the back of the present device 30 and is contoured to mirror and engage with the shape of the user's thoracic kyphosis and lumbar lordosis. The monolithic rigid plate 12, which may comprise any convenient material such as plastic, metal or so forth, is substantially fixed in its position by any convenient means. Thus it may be directly connected at its top to a portion of the strapping 16, or in another approach as may be seen in FIG. 5, the plate 12 can be positioned in a pocket formed at the interior of panel 23. In any of these arrangements the plate 12 is effectively secured between the tensioned strapping means 16 and encirclement means 22 (connected to back panel 23), in consequence of which the upward and forward directed forces from the tensioned strapping press the rigid plate toward the spine of the user to exert beneficial pressure against the thoracic kyphosis and lumbar lordosis to relieve back strain.

It will also be noted that an extension support 15 is provided at the rear of the strapping as an addition which may be used for taller individuals who use the present device. In another feature of the device surface pads comprising a compressible foam can be provided between the rigid plate 12 and the back of the user as seen at 13. Additionally, multiple cell air bladders 14 can be present at the lower lordosis region and can utilize one or many segmented air chambers and/or rigid foam pads which can be fixed in their volume. Where plural air bladders are used they can be individually adjustable to provide a desired degree of support against specific vertebrae with which they are associated.

Figure 5:
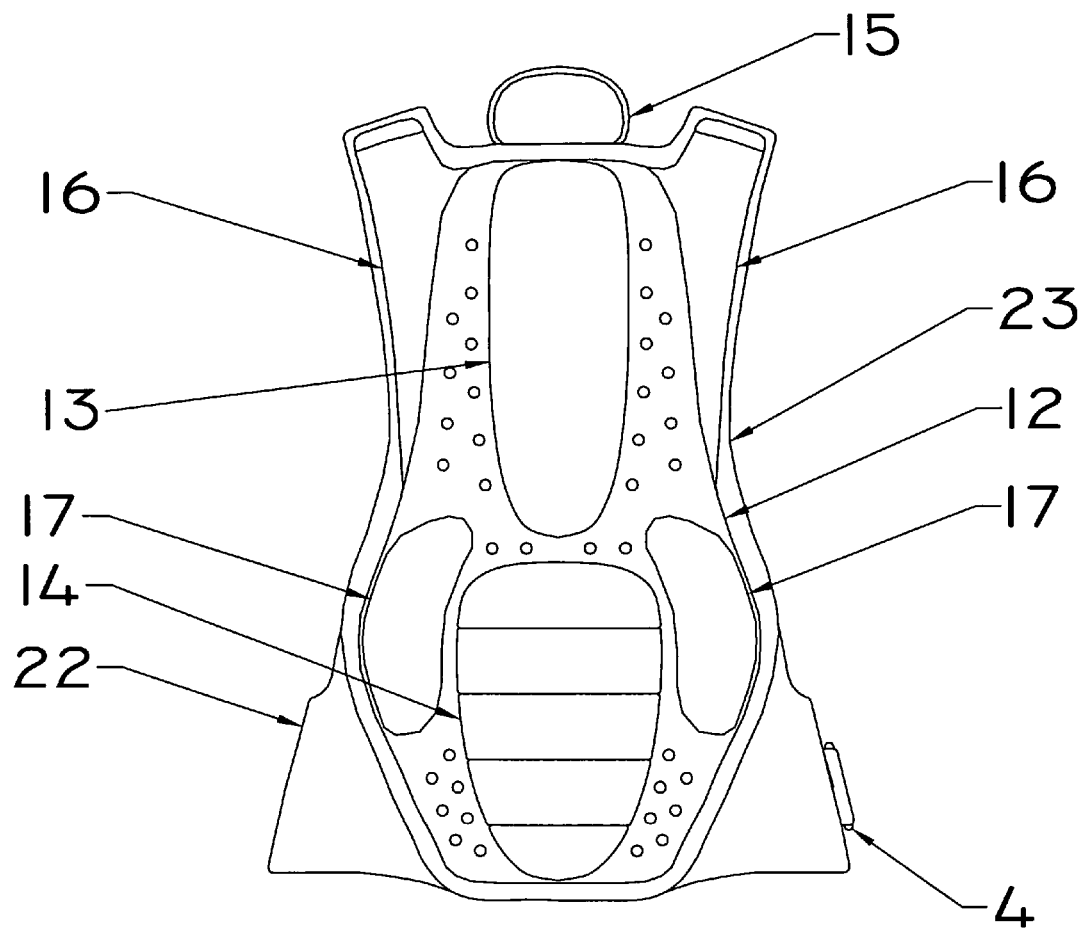
FIG. 5 depicts the internal positions of contact pads (foam) and lordosis pad of the FIG. 1 device.

Also as best seen in FIG. 5, side support contact pads formed of foam or even air bladders, can be provided at 17 to provide yet further comfort and support for the user.

Figure 6:
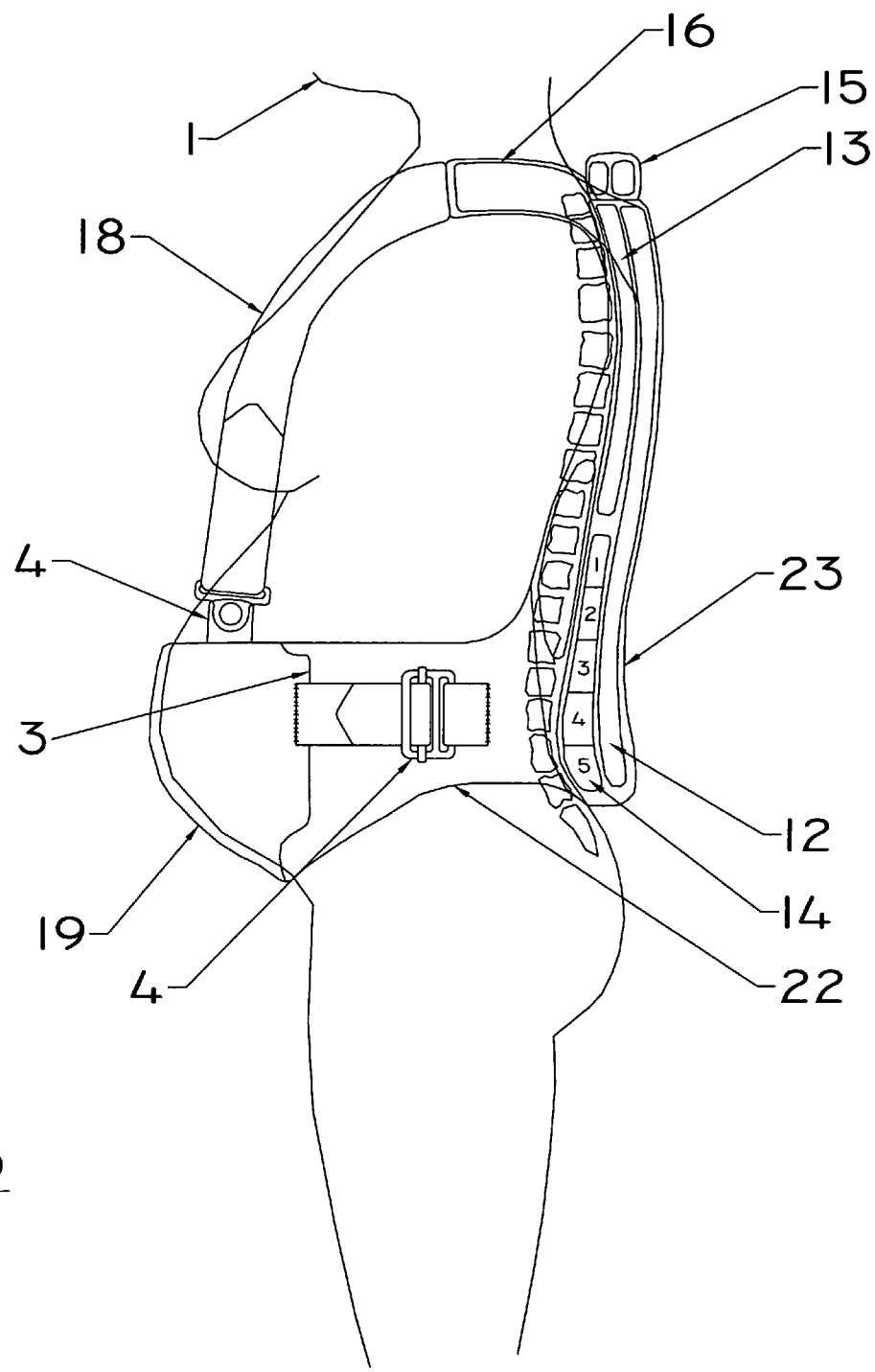
FIG. 6 is similar to FIG. 2, but shows an embodiment of the device suitable for use by a pregnant woman to assist in ameliorating the effects of the abdominal weight being carried by her.

In FIG. 6 a further embodiment of the invention is shown. In this instance the weight support means comprises a front abdominal lift pad 19 which is designed and intended for use in supporting via lift straps 18 the abdominal region of a pregnant woman, particularly during the latter phases of pregnancy when the off axis weight from the enlarged abdomen create great strain upon the spine and associated musculature. The principles of the invention as shown in this Figure are substantially identical to those described in connection with the prior Figures.

Figure 7:
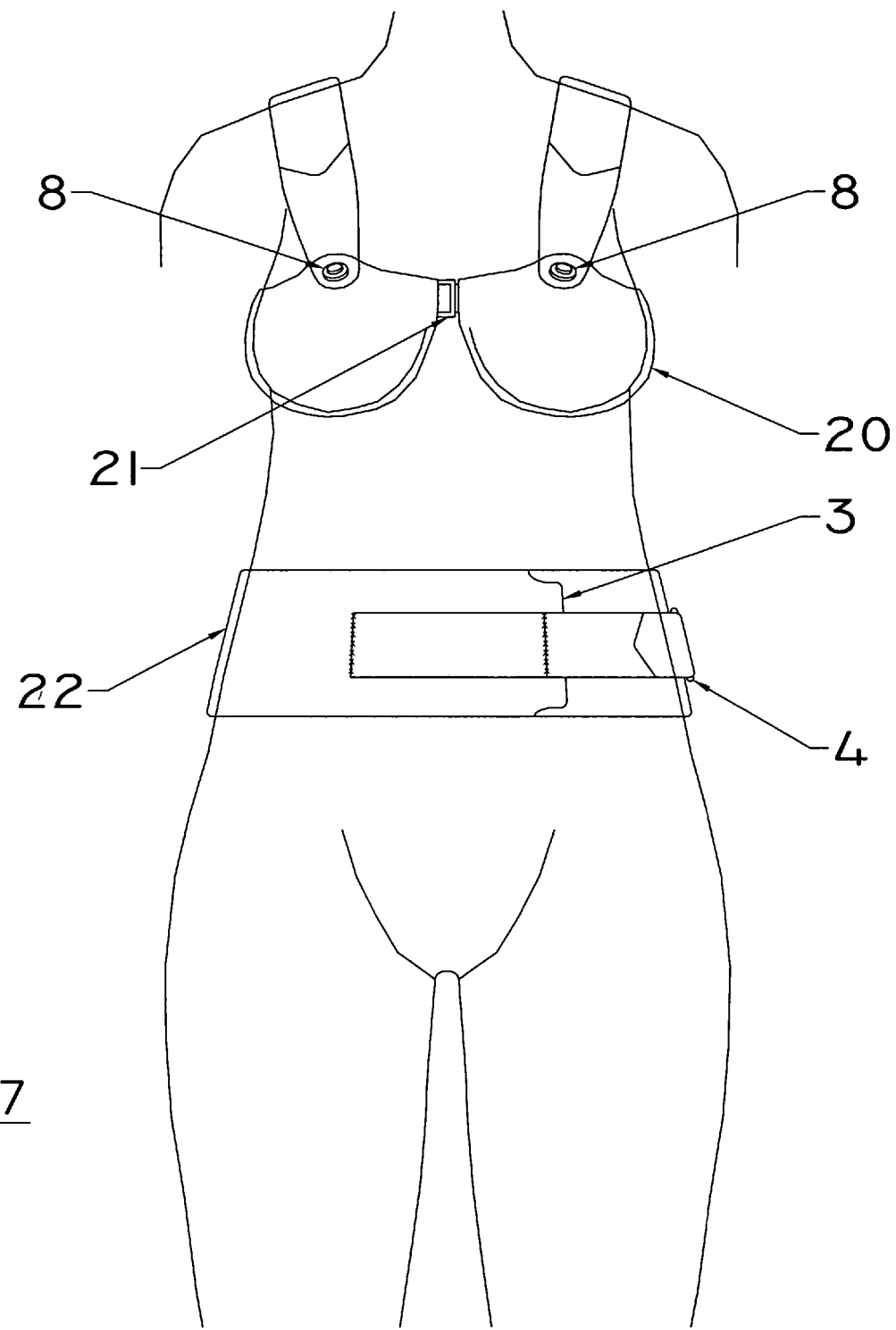
FIGS. 7 and 8 are similar to FIGS. 1 and 2, but show an embodiment of the device intended for use by a woman having large breasts.
Figure 8:
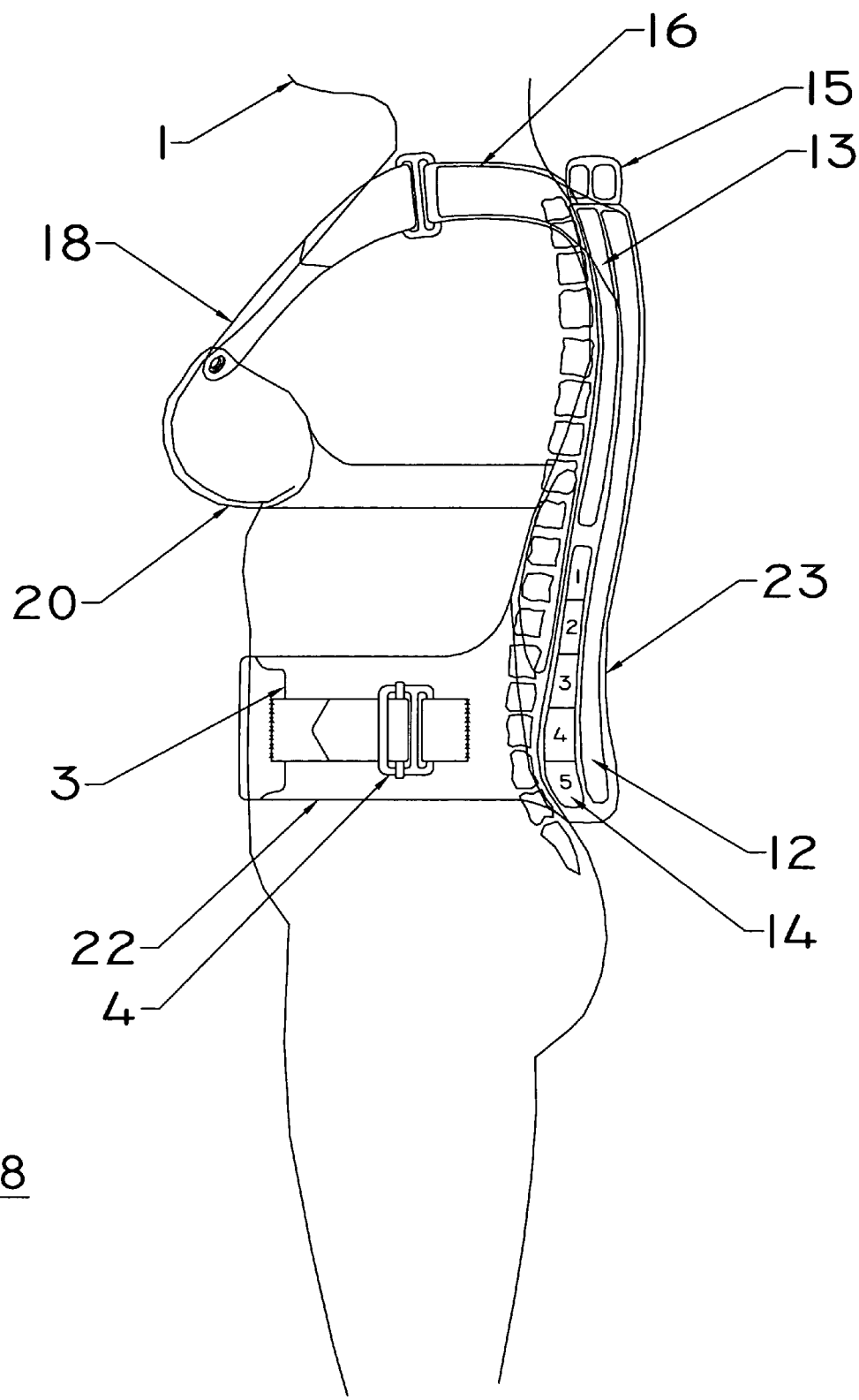

In FIG. 7 and FIG. 8 a yet further embodiment of the invention is shown. In this instance a lift support brassiere 20 comprises the weight support means. The device is provided with a front latch buckle 21 and the waist encirclement means comprises the main strap 22. The arrangement and structure from a mechanical viewpoint is substantially identical in its principles to the device previously described in the prior Figures, except that in this instance the off axis weight causing the discomfort (and even injury) to the user arises from the large weighty breasts associated with a large breasted woman.

While the present invention has been set forth in terms of specific embodiments thereof, the instant disclosure is such that numerous variations upon the invention are now enabled to those skilled in the art, which variations yet reside within the scope of the present teaching. Accordingly, the disclosure is to be broadly construed and limited only by the scope and spirit of the claims now appended hereto.

The invention claimed is:

1. A device for relieving back strain for a user who is supporting a substantial weight which is off the user's vertical body axis at his or her front side, comprising:
    a waist encirclement means securable about the waist of the user;
    a monolithic rigid plate contoured to mirror and engage with the shape of the thoracic kyphosis and lumbar lordosis, said plate being positioned at the back of the user, and restrained in its degree of possible upward displacement by said waist encirclement means;
    flexible strapping means connected directly or indirectly to said plate at the rear of the user, the plate thereby being effectively secured between the strapping means and the said waist encirclement means, whereby an upward and forward force is exerted at the said plate when the said strapping means is tensioned;
    said strapping means extending over the shoulders from the rear side of the user; and
    weight support means being secured to the strapping means at the front of the user for supporting the off-axis weight, said flexible strapping means bearing a substantial part of the weight imposed upon the weight support means and therefore being tensioned by the weight;
    whereby the resulting forces generated by the tensioned strapping means act to press the contoured plate toward the user's back, to thereby exert beneficial pressure against the thoracic kyphosis and lumbar lordosis to relieve the back strain.

2. A device in accordance with claim 1, wherein said strapping means is connected directly to said rigid plate.

3. A device in accordance with claim 1, further including a back panel extending upwardly from the rear side of the waist encirclement means with the flexible strapping means extending from the back panel, and wherein said strapping means exerts said force on said rigid plate by being indirectly attached to said plate via said back panel.

4. A device in accordance with claim 1, further including cushioning material between said rigid plate and the back of the user.

5. A device in accordance with claim 4, wherein said cushioning material comprises one or more air bladders which are adjacent at least the lordosis region of the user.

6. A device in accordance with claim 4, further including cushioning material between the waist encirclement means and the sides of the user.

7. A device in accordance with claim 1, wherein said weight support means comprise a baby or infant carrier.

8. A device in accordance with claim 1, wherein said weight support means comprises an abdominal support for use by a pregnant woman.

9. A device in accordance with claim 8, wherein said abdominal support is formed at the front side of said waist encirclement means.

10. A device in accordance with claim 1, wherein said weight support means comprises a brassiere for a large-breasted woman.

11. A device for relieving back strain for a user who is supporting a substantial weight which is off the user's vertical body axis at his or her front side, comprising:
    waist encirclement means securable about the waist of said user;
    a back panel extending upwardly from the rear side of said waist encirclement means;
    flexible strapping means extending from said back panel over the shoulders of the user and extending down the front of said user;
    weight support means secured to said strapping means at the front of said user for supporting said weight;
    said flexible strapping means bearing a substantial part of the weight of said support means and being tensioned from said weight and in turn tensioning said back panel; and
    a monolithic rigid plate positioned behind and adjacent to the spine of the said user, said plate being contoured to mirror and engage with the shape of the thoracic kyphosis and lumbar lordosis, said plate being restrained in its degree of possible upward displacement by said waist encirclement means; the tensioned strapping means and back panel being positioned relative to said plate such that user-directed forces generated from the tensioned strapping means and panel act to press said plate toward the user's back to exert beneficial pressure against said thoracic kyphosis and lumbar lordosis to relieve said back strain.

12. A device in accordance with claim 11, wherein the bottom of said weight support means is secured to said waist encirclement means.

13. A device in accordance with claim 11, wherein said weight support means comprise a baby or infant carrier.

14. A device in accordance with claim 11, wherein said weight support means comprises an abdominal support for use by a pregnant woman.

15. A device in accordance with claim 14, wherein said abdominal support is formed at the front side of said waist encirclement means.

16. A device in accordance with claim 11, wherein said weight support means comprises a brassiere for a large-breasted woman.

17. A device for relieving back strain for a user who is supporting a substantial weight which is off the user's vertical body axis at his or her front side, comprising:
    a waist encirclement piece securable about the waist of said user;
    a back panel having an interior void space, said panel extending upwardly from the rear side of said waist encirclement piece and forming shoulder straps for passing over the shoulders of the user, said straps extending down the front side of the user;
    weight support means secured to said straps at the front of the said user for supporting said weight, said strapping thereby bearing a substantial part of the said weight of said support means and being thereby tensioned from said weight and tensioning the said back panel; and
    a monolithic rigid plate contoured to mirror and engage with the shape of the thoracic kyphosis and lumbar lordosis, said plate being positioned in said interior void of said back panel and thereby in proximity to the user's back; said plate being restrained in its degree of possible upward displacement by said back panel by being effectively secured between the tensioned straps and encirclement piece; the tensioned straps and back panel acting to press said plate toward the user's back to exert beneficial pressure against said thoracic kyphosis and lumbar lordosis to relieve said back strain.

18. A device in accordance with claim 17, wherein the said void at said back panel extends to portions of said formed straps which adjoin said panel and overlie the user's shoulders, and wherein said panel includes portions at its upward end extending into the void regions of said straps.

19. A device in accordance with claim 17, wherein said weight support means comprises a baby or infant carrier, and wherein the bottom of said carrier is connected to the front of said encirclement means.

20. A device in accordance with claim 17, wherein said weight support means comprises an abdominal support for use by a pregnant woman.

21. A device in accordance with claim 20, wherein said abdominal support is formed at the front side of said encirclement piece.

22. A device in accordance with claim 17, wherein said weight support means comprises a brassiere for a large-breasted woman.

23. A device for relieving back strain for a user who is supporting a substantial weight which is off the user's vertical body axis at his or her front side, comprising:
  strapping means restrained at the rear of said user by said encirclement means, the non-restrained end of said strapping means extending over the shoulders and down the front of said user;
  weight support means secured to said strapping means at the front of said user for supporting said off-axis weight;
  said strapping means being tensioned from said weight; and
  a monolithic rigid plate contoured to mirror and engage with the shape of the thoracic kyphosis and lumbar lordosis being positioned behind the spine of the said user and being interconnected to said tensioned strapping means and said user so that user-directed forces generated from the tensioned strapping means acts to press said plate toward the user's back to exert beneficial pressure against said thoracic kyphosis and lumbar lordosis to relieve said back strain.

24. A device in accordance with claim 23, wherein said weight support means comprise a baby or infant carrier.

25. A device in accordance with claim 23, wherein said weight support means comprises an abdominal support for use by a pregnant woman.

26. A device in accordance with claim 23, wherein said weight support means comprises a brassiere for supporting the breasts of a large-breasted woman.

* * * * *